United States Patent [19]

Abuknesha

[11] Patent Number: 5,225,516

[45] Date of Patent: Jul. 6, 1993

[54] POLYMERS

[75] Inventor: Ramadan A. Abuknesha, London, England

[73] Assignee: The General Electric Company, p.l.c., England

[21] Appl. No.: 617,019

[22] Filed: Nov. 21, 1990

[30] Foreign Application Priority Data

Nov. 22, 1989 [GB] United Kingdom ................. 8926407

[51] Int. Cl.$^5$ ............................................ C08L 67/02
[52] U.S. Cl. .................................... 528/176; 528/183; 528/184; 528/185; 530/403; 435/4; 436/537; 436/546; 422/61
[58] Field of Search ............... 528/176, 183, 184, 185; 530/403; 522/625; 435/4; 436/537, 546; 422/61

[56] References Cited

U.S. PATENT DOCUMENTS 4,325,903 4/1982 Wissbrun ............................ 528/176

*Primary Examiner*—Maurice J. Welsh
*Attorney, Agent, or Firm*—Kirschstein, Ottinger, Israel & Schiffmiller

[57] ABSTRACT

The invention provides a polymer comprising a chain of detectable units joined together by linker arms.

The detectable units may be, for example, antigenic or form part of a fluorescent or chemiluminescent or chromogenic or enzyme signal system.

The polymer may find an application in the assay of an analyte which is a member of a specific binding pair.

The invention also provides a labelled reagent in which the reagent is a member of a specific binding pair and the label is a polymer in accordance with the invention. The invention further provides an assay involving the use of a labelled reagent in accordance with the invention. Also the invention provides a kit for performing an assay, which kit includes a supply of a labelled reagent in accordance with the invention.

14 Claims, 4 Drawing Sheets

STEP 1

STEP 2

F

J

H

L

M

N

Rhodamine

POLYMERS

This invention provides new polymers which are particularly suitable for use in the assay of an analyte which is a member of a specific binding pair. Assays of this kind are well known and widely used. Examples of specific binding pairs include antigen (hapten)/antibody; sugar/lectin; biotin/avidin (streptavidin); DNA(RNA) chain/complementary DNA(RNA) chain; enzyme/substrate.

These assays typically involve the use of a labelled reagent, in which the reagent is a member of the specific binding pair. The reagent may be radioactively labelled, or labelled by attachment to a detectable unit which may be antigenic or may form part of a fluorescent or chemiluminescent or chromogenic or enzyme signal system. Usually, the reagent has one or more reactive sites, and a monomeric detectable unit is attached to the or each reactive site.

The sensitivity of such assays would be increased if many detectable units were attached to the or each reactive site of the reagent molecule. It is an object of this invention to achieve improved assay sensitivity in this way.

In one aspect the invention provides a polymer comprising a chain of detectable units joined together by linker arms. Preferably the polymer consists of a chain ababab. . . , in which a is a detectable unit and b is a linker arm. The number of units in the polymer is not critical. In principle assay sensitivity may be doubled by the use of a polymer containing only two detectable units. Thus, as used in this Specification the term "polymer" embraces, inter alia, polymers which may be considered to be oligomers.

Almost all units are detectable if enough care is taken. Units that are readily detectable, such as those conventionally used as labels in assays such as those discussed above may be utilised in accordance with the present invention. Preferably the detectable units are antigenic or form part of a fluorescent or chemiluminescent or chromogenic or enzyme signal system. Particularly preferred are fluorescent units such as those based on fluorescein or coumarin. To incorporate the detectable unit in a polymer chain, some chemical modification will usually be needed. It is, of course, essential that this chemical modification does not inhibit the property by which the unit is detectable. For example, when the detectable unit is a fluorescent species, it is essential that this be capable of fluorescing even after incorporation in the polymer. Ways in which various detectable units can be chemically modified without inhibiting their detectable properties are well-known in the art and will not be described here.

The linker arm joins the detectable units together. It is preferably rigid, by virtue of containing an aromatic or cyclic group or ethylenic unsaturation. It is preferably long, e.g. at least three carbon atoms in a length and often much longer. It thus holds the detectable units in spaced-apart configuration, so that a reaction of one unit in the chain (in the course of detection) is not unduly inhibited by adjacent units. Linker arms are well known in the art.

Particularly if the detectable unit is hydrophobic, the linker arm is preferably hydrophilic to an extent necessary to render the polymer water-soluble. Water-insoluble polymers may be useful for some purposes, but are not suitable for most assay systems. A preferred linker unit is based on a 1,4-di(aminoalkyl)piperazine, where the alkyl group may typically contain 2 to 12 carbon atoms. Less preferred are linker arms based on di(aminoalkanes) where the amino groups are attached to the ends of an alkyl chain of typically 2 to 12 carbon atoms.

Preparation of the polymers may be effected by standard techniques. For example, if the detectable unit can be modified to provide two carboxylic acid groups, or one carboxylic acid group and one amino or thiocyanate group, polymerisation may be effected by known conjugation methods such as peptide condensing reagents, dialdehydes or by the standard techniques used in protein chemistry to prepare polypeptides from amino acids. Attachment of one end of the chain to a solid support might be used to ensure that linear polymers are formed to the exclusion of circular ones.

The invention also provides a labelled reagent in which the reagent is a member of a specific binding pair and the label is a polymer as described. The chemistry involved in labelling reagents with polymeric labels is essentially the same as that used with monomeric labels. The labelled reagent may then be used in an assay for a member of the specific binding pair in conventional manner. This invention includes kits for performing such assays which include a supply of the labelled reagent.

It is to be understood that, in accordance with the present invention, the detectable units form part of the polymer chain (i.e. part of the backbone" of the polymer chain).

This contrasts with polymers in which detectable units are merely appended to a polymer chain.

Polymers in which the detectable units form part of the polymer "backbone" may offer certain advantages.

For example, the spacing of one detectable unit from another may be controlled. Also, for example, the polymer chain length may be controlled. Also, by way of further example, the solubility of the polymer may be controlled (e.g. the polymer may be made insoluble or soluble to a greater or a lesser extent; this may be achieved, for example, by controlled introduction of polarity).

It is to be understood that without control of the spacing of detectable units with respect to one another problems may occur, for example, due to "self-quenching" and/or the inclusion of detectable units in hydrophobic "pockets"; such problems may give rise to unpredictable and irreproducible responses in assays.

Also, for example, it is to be understood that without control of polymer chain length reproducibility in assay responses may be impaired.

Further, for example, it is to be understood that the control of solubility may facilitate the production of a polymer of substantial chain lengths which still has a useful solubility (e.g. in water of aqueous media).

BRIEF DESCRIPTION OF DRAWINGS

Reference is directed to the accompanying drawings in which:

FIG. 1 shows a labelled reagent according to the invention. The reagent is an antigen. The label is a polymer comprising four detectable units, joined together (and joined to the antigen) by means of four linker arms. The detectable units A are derived from 7-hydroxy-8-carboxy-4-methylcoumarin-3-acetic acid. The linker arms B are derived from 1,4-bis(3-aminopropyl)piperazine.

FIG. 2 shows the steps involved in the preparation of this reagent. 2-6-dihydroxybenzoic acid (C) and diethylacetylsuccinate (D) are reacted in the presence of concentrated sulphuric acid to form the ethyl ester, which is converted by KOH to 7-hydroxy-8-carboxy-4-methylcoumarin-3-acetic acid (F). Step 2 involves forming the N-hydoxysuccinimidyl ester of F (G). Step 3 involves polymerisation of G with 1,4-bis(3-aminopropyl)piperazine (H) at pH 8.6 to give a linear polymer I. Step 4 involves reacting this linear polymer with the antigen to give the reagent shown in FIG. 1.

FIG. 3 shows six variations on the coumarin structure, lettered F, J, K, L, M and N. All contain two carboxylic acid groups. In compounds M and N, a carboxylic acid group may be present at the 6-position or the 8-position, and this is indicated by arrows at both positions. Other variations in the coumarin structure are possible.

FIG. 4 shows the preparation of various detectable units based on fluorescein. 2,6-dihydroxybenzoic acid (P) is reacted with a phthalic acid derivative (Q), in which the aromatic ring carries a substituent R. Various products are possible, depending on the nature of R; when this is a $NO_2$ group, this can be reduced to $NH_2$ and thence to NCS to facilitate linkage of the fluorescein derivative in the polymer.

EXAMPLE 1

Equimolar quantities of 2,6-dihydroxybenzoic acid (see C of FIG. 2 of the accompanying drawings) and diethylacetylsuccinate (see D of FIG. 2) were mixed, conc. $H_2SO_4$ was added, and the resulting mixture was left overnight to produce an ethyl ester.

The ethyl ester was precipitated from the mixture by adding to cold distilled $H_2O$. The precipitated ethyl ester was separated and washed on a filter and then purified; (purification may be effected e.g. by crystallization or column chromatography on silica gel).

Approximately 5 gm of the ethyl ester was mixed with 5% methanolic KOH and left overnight at 50° C.; subsequently methanol was removed using a rotary evaporator under vacuum and compound F (see FIG. 2) was obtained after precipitation by addition of 1M HCl and filtration and washing.

EXAMPLE 2

Figure 1:
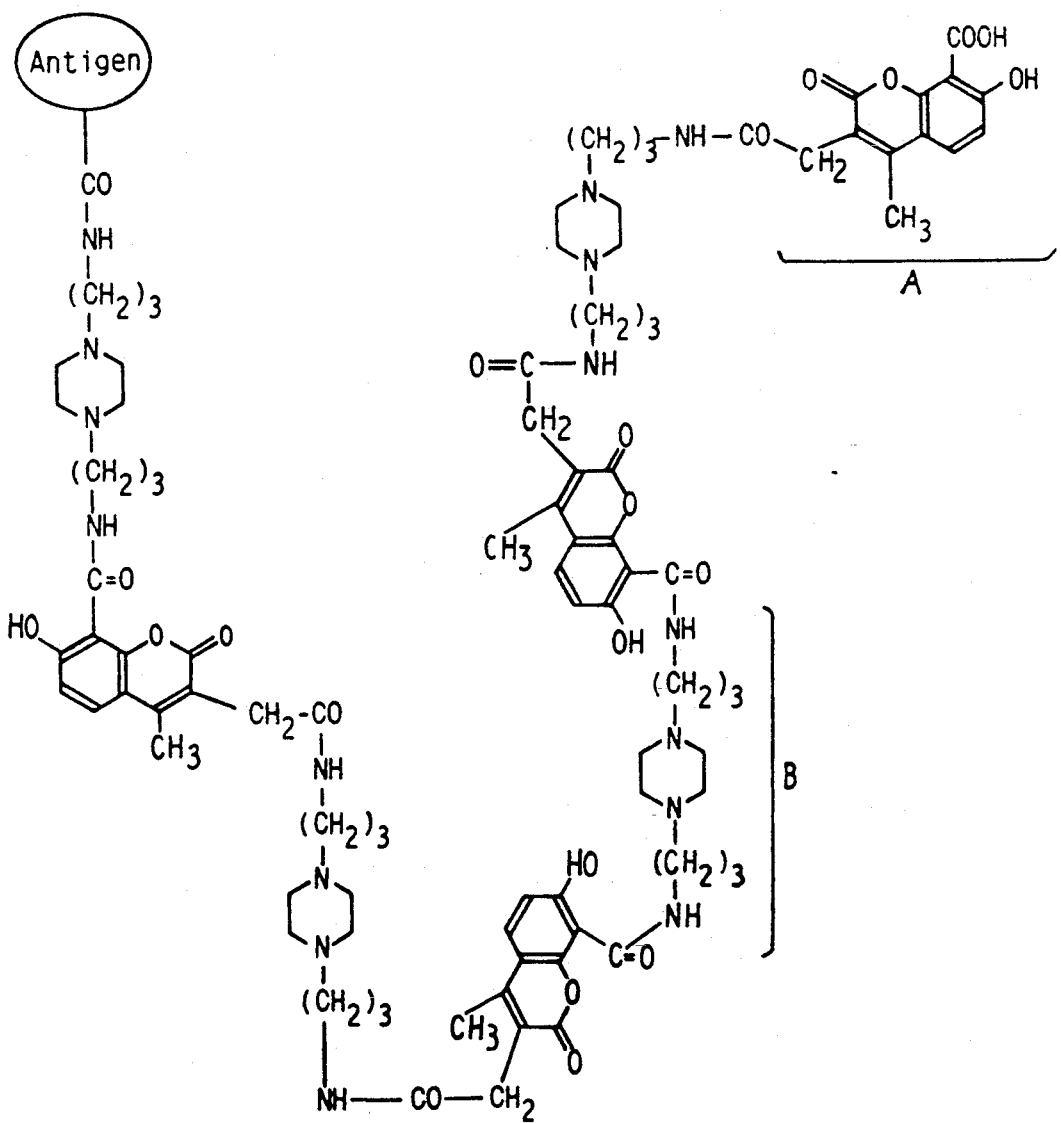
FIG. 1 shows the structure of a polymer according to the invention based on 7-hydroxycoumarin.
Figure 2:
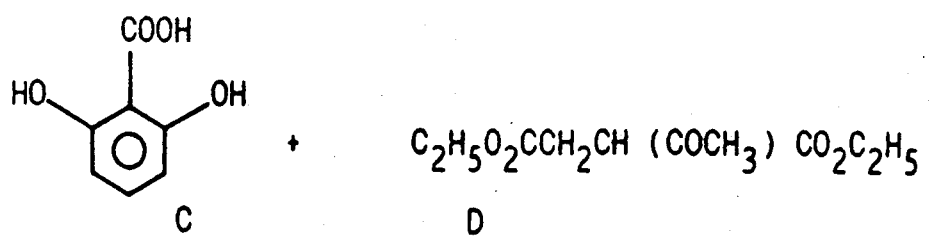
FIG. 2 shows the steps involved in the preparation of the polymer shown in FIG. 1.
Figure 2:
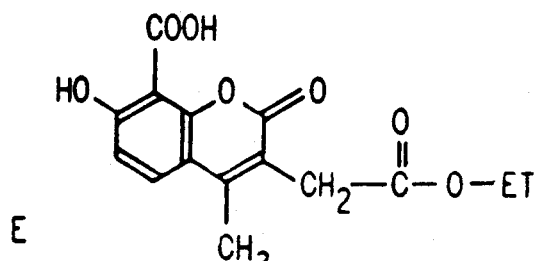
Figure 2:
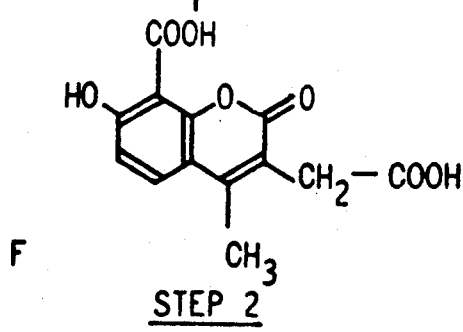
Figure 2:
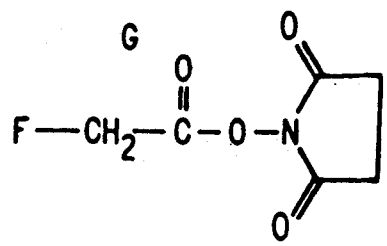

Compound F was treated to give the N-hydroxysuccinimidyl ester of F (i.e. compound G of FIG. 2).

Compound G was added in aliquots over a period of 2 hours to compound H, at pH 8.6 in the presence of sodium tetraborate, so that polymerisation occurred to give the linear polymer (oligomer) I.

EXAMPLE 3

Figure 3:
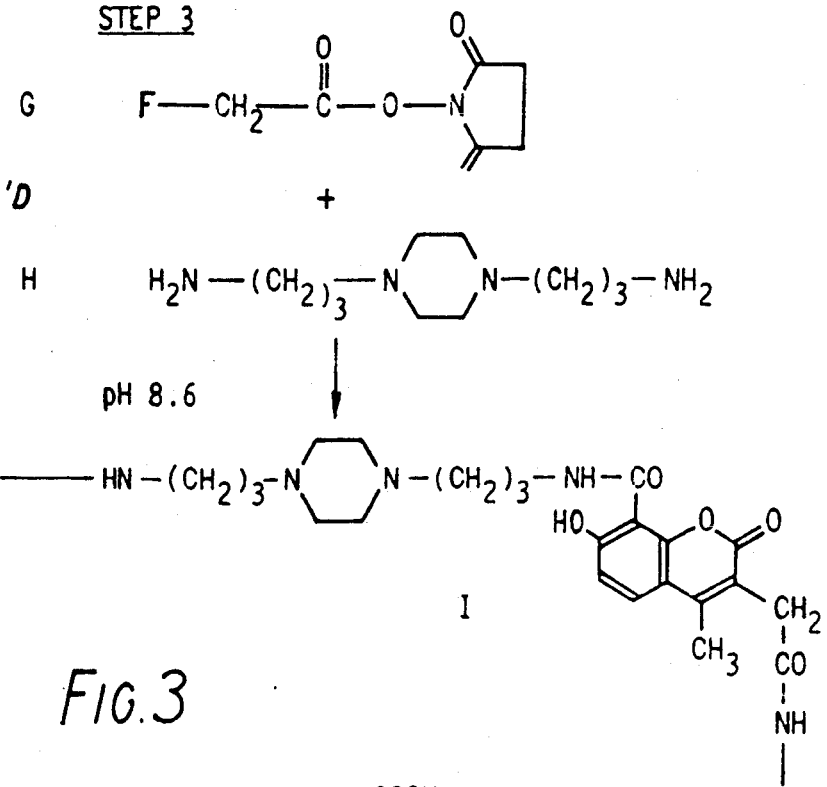
FIG. 3 shows examples of variations of the coumarin structure which may be used in polymer preparation.
Figure 3:
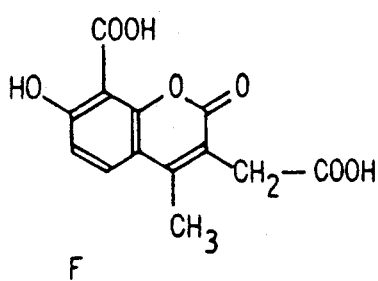
Figure 3:
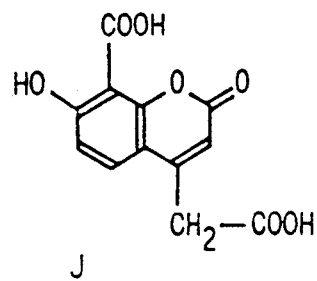
Figure 3:
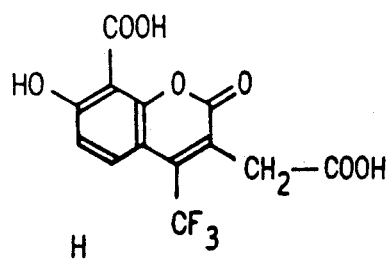
Figure 3:
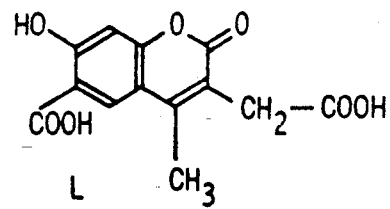
Figure 3:
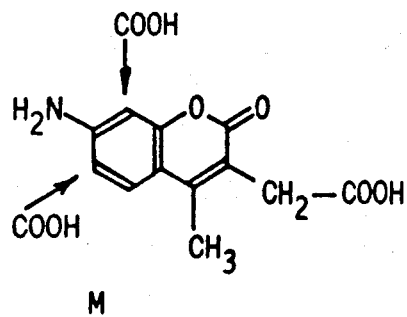
Figure 3:
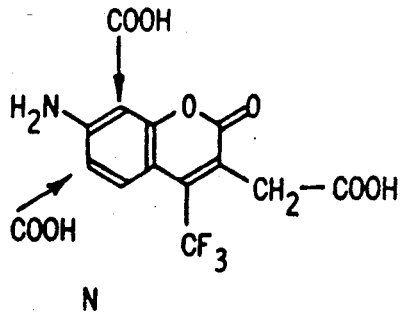
Figure 4:
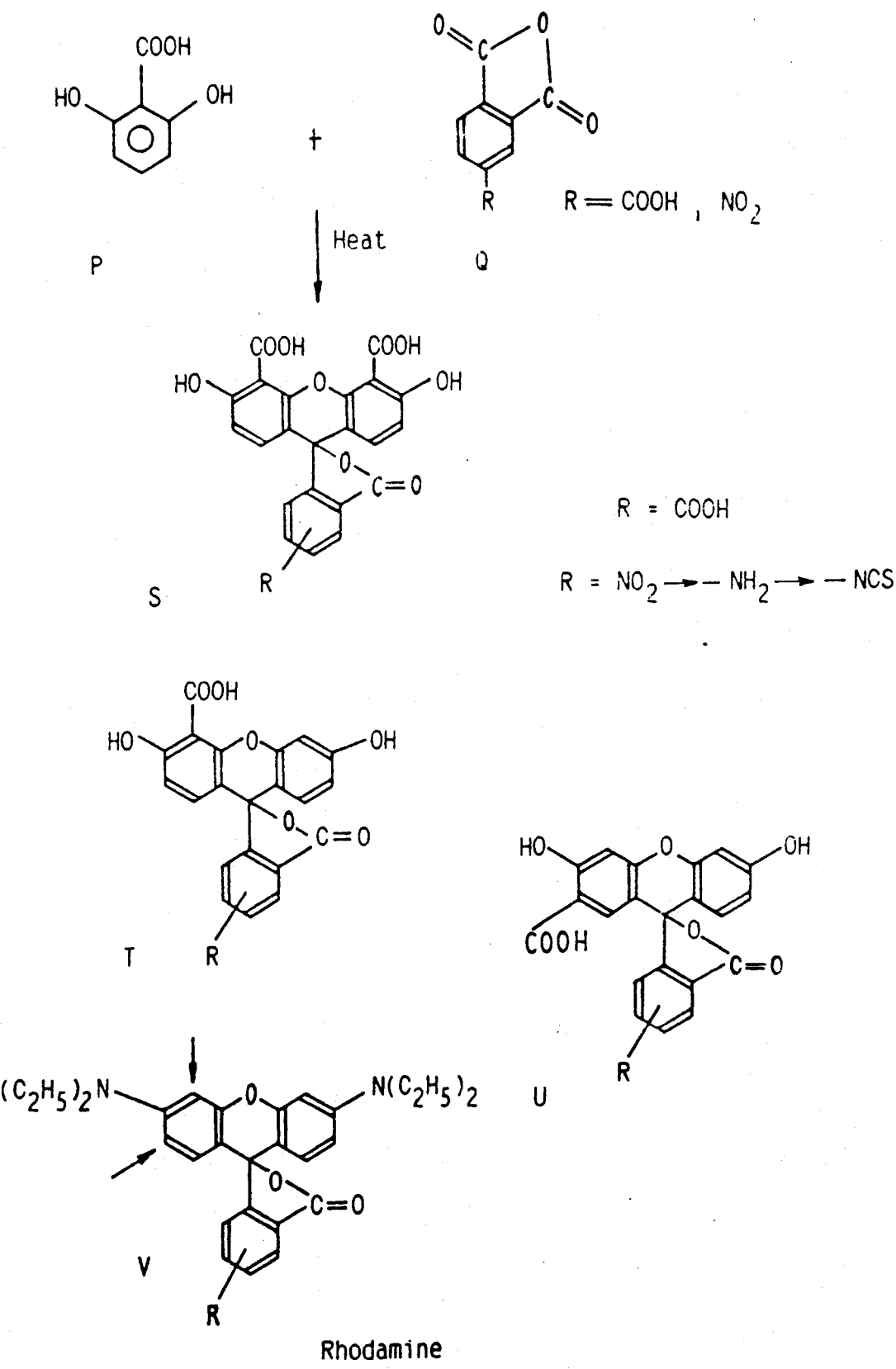
FIG. 4 shows variations of the fluorescein structure which may be used in polymer preparation.

Compound J (of FIG. 3 of the accompanying drawings) was prepared in a manner analogous to the preparation of compound F in Example 1.

EXAMPLE 4

Compound J was treated to form a linear polymer in a manner analogous to the treatment of compound F in Example 2.

EXAMPLE 5

The polymer preparation reaction mixtures of Examples 2 and 4 were analysed for the presence of high molecular weight polymers.

Two techniques were used:
(a) gel filtration chromatography on a Sephadex G50 column; in this technique 1.5 ml of the reaction mixture was chromatographed on a 50×1.5 cm column equilibrated with sodium tetraborate buffer (at pH 9.0) with a flow rate of 45 ml/hr and collecting fractions of 1.8 ml.
(b) reaction mixture was concentrated, clarified of insoluble material and dialysed (using Visking tubes) against 5 l of sodium bicarbonate/carbonate buffer (pH 8.5) for 3 to 7 days (changing dialysis buffer daily); the resulting material was then chromatographed as described in (a) above.

The absorption at 360 nm and fluorescence (ex. 370 nm floro. 470 nm) of the column fractions were measured. In all cases tested there were peaks in the column void volumes (unretarded materials) indicating that the molecular weight of the constituents was 50000 and above.

Lower molecular weight materials were eluted in larger peaks which came through the column at a later stage.

It is to be noted that dialysis is expected to remove the small molecular weight substituents (e.g. less than 10000–12000) and retain within the dialysis membrane large molecular weight materials which are recovered.

The high molecular weight peaks obtained from several column runs were pooled, analysed by scanning at 220–700 nm and inspected for the level of fluorescence (qualitative assessment).

These materials showed absorption profiles similar to the starting fluorochrome units (peak at 360 nm) with high levels of characteristic bright blue fluorescence.

Both the absorption and fluorescence levels were pH dependent showing maximum adsorption and fluorescence at pH 9.8–10.3.

EXAMPLE 6

Polymer prepared as in Example 2 (i.e. compound I) was used for conjugation to a steroid hapten.

Thus, the steroid derivative 17-α-hydroxyprogesterone-3-carboxymethyloxime was activated by derivitization to its N- hydroxysuccimidyl derivative (active ester); this derivative (500 μg) was added (in 100 μl dioxane) to a solution of polymer I (20 mg in 2 ml sodium bicarbonate buffer; pH 8.6) and allowed to react for 2 hrs at ambient temperature.

The resulting reaction mixture was chromatographed on a Sephadex G25 column. Initial peaks from the chromatographic procedure containing high molecular weight materials were collected.

EXAMPLE 7

The procedure of Example 6 was followed by the exception that the steroid derivative used was 17-β-estradiol-3-carboxymethyl ether.

EXAMPLE 8

An antibody (IgG preparation) to 17-α-hydroxyprogesterone was isolated from sheep antiserum and coupled to commercially available micro-cellulose magnetisable particles by cyanogen bromide activation according to protocols found in the literature.

EXAMPLE 9

The procedure of Example 8 was followed with the exception that an antibody (IgG preparation) to 17-β-estradiol was isolated from sheep antiserum and coupled to commercially available micro-cellulose magnetisable particles.

EXAMPLE 10

An aliquot of the antibody coupled particles prepared as in Example 8 (50 μl containing approximately 20 μg particle suspension in 10 mM phosphate buffer; pH 7.2 with 0.1M NaCl, 0.2% gelatin) was mixed with an aliquot of the polymer-hapten preparation prepared as in Example 6 (100 μl) by shaking, for 30 minutes; the particles were washed 3 times with buffer and then left for 15 minutes with 500 μl of 0.1M glycine-NaOH buffer (pH 10.4) containing 20% acetonitrile. (It is to be understood that the high pH buffer with acetonitrile is known to elute antibody bound hapten.)

After allowing the particles to settle (using a magnetic plate) the fluorescence in the eluted supernatant was measured. Substantial levels of fluorescence were found when compared with control experiments.

This confirms that the polymer-hapten preparation contained covalently coupled immunologically active hapten.

EXAMPLE 11

The procedure of Example 10 was followed with the exception that the antibody coupled particles used were those prepared as in Example 9 and the polymer-hapten preparation was that prepared as in Example 7.

Fluorescence observations confirmed that the polymer-hapten preparation contained covalently coupled immunologically active hapten.

EXAMPLE 12

An antibody coupled to magnetisable particles was used as a solid phase antibody partner in an assay; the assay was a fluoro-immunoassay method using a polymer-hapten preparation (as prepared in accordance with Example 6) as a fluorescent tracer.

Thus suitable dilutions of the antibody and the polymer-hapten preparation were found such that the presence 10 ng of competitor hapten (17-α-hydroxyprogestrone) would inhibit the binding of more than 80% of the tracer.

Standard curves were constructed from experiments in which the level of the competitor hapten was increased from zero to 10 ng/assay tube.

EXAMPLE 13

The procedure of Example 12 was followed with the exception that the polymer-hapten preparation was as prepared in Example 7 and the competitor hapten was 17-β-estradiol.

I claim:
1. A polymer comprising a chain of detectable units joined together by linker arms.
2. A polymer as claimed in claim 1, wherein the linker arms are so hydrophilic that the polymer is water-soluble.
3. A polymer as claimed in claim 1, wherein the linker arms comprise a 1,4-di(aminoalkyl)piperazine.
4. A polymer as claimed in claim 1, wherein the detectable units are antigenic.
5. A polymer as claimed in claim 1, wherein the detectable units form part of a fluorescent signal system.
6. A polymer as claimed in claim 1, wherein the detectable units form part of a chemiluminescent signal system.
7. A polymer as claimed in claim 1, wherein the detectable units form part of a chromogenic signal system.
8. A polymer as claimed in claim 1, wherein the detectable units form part of an enzyme signal system.
9. A polymer as claimed in claim 5, wherein the detectable units are fluorescent.
10. A polymer as claimed in claim 9, wherein the detectable units are based on fluorescein.
11. A polymer as claimed in claim 9, wherein the detectable units are based on coumarin.
12. A labelled reagent in which the reagent is a member of a specific binding pair and the label is a polymer comprising a chain of detectable units joined together by linker arms.
13. An assay for a member of a specific binding pair involving the use of a labelled reagent in which the reagent is a member of the specific binding pair, wherein the labelled reagent is a labelled reagent in which the reagent is a member of a specific binding pair and the label is a polymer comprising a chain of detectable units joined together by linker arms.
14. A kit for performing an assay for a member of a specific binding pair involving the use of a labelled reagent in which the reagent is a member of the specific binding pair wherein the labelled reagent is a labelled reagent in which the reagent is a member of a specific binding pair and the label is a polymer comprising a chain of detectable units joined together by linker arms, which kit includes a supply of a labelled reagent comprising a labelled reagent in which the reagent is a member of a specific binding pair and the label is a polymer comprising a chain of detectable units joined together by linker arms.

* * * * *